United States Patent
Sullivan et al.

(10) Patent No.: US 7,304,580 B2
(45) Date of Patent: Dec. 4, 2007

(54) INTELLIGENT MEDICAL VIGILANCE SYSTEM

(75) Inventors: Patrick K. Sullivan, Kailua, HI (US); Matthew S. Glei, Honolulu, HI (US); Paul M. Embree, Honolulu, HI (US)

(73) Assignee: Hoana Medical, Inc., Honolulu, HI (US)

( * ) Notice: Subject to any disclaimer, the term of this patent is extended or adjusted under 35 U.S.C. 154(b) by 270 days.

(21) Appl. No.: 11/004,589

(22) Filed: Dec. 3, 2004

(65) Prior Publication Data

US 2005/0190062 A1 Sep. 1, 2005

Related U.S. Application Data

(60) Provisional application No. 60/526,612, filed on Dec. 4, 2003.

(51) Int. Cl.
*G08B 23/00* (2006.01)

(52) U.S. Cl. .............. 340/573.1; 340/573.5; 340/575; 340/576; 340/511; 340/539.12; 600/300; 600/484; 600/537

(58) Field of Classification Search ............ 340/573.1, 340/573.5, 575, 576, 511, 539.12; 600/300, 600/484, 537

See application file for complete search history.

(56) References Cited

U.S. PATENT DOCUMENTS

| | | | |
|---|---|---|---|
| 4,320,766 A | 3/1982 | Alihanka et al. | |
| 4,509,527 A | 4/1985 | Fraden | |
| 4,562,723 A * | 1/1986 | Hubner | 73/31.07 |
| 4,827,763 A | 5/1989 | Bourland et al. | |
| 4,926,866 A | 5/1990 | Lee | |
| 5,002,060 A | 3/1991 | Nedivi | |
| 5,137,033 A | 8/1992 | Norton | |
| 5,144,284 A | 9/1992 | Hammett | |
| 5,292,340 A * | 3/1994 | Crosby et al. | 607/17 |
| 5,353,793 A | 10/1994 | Bornn | |
| 5,416,469 A | 5/1995 | Colling | |

(Continued)

FOREIGN PATENT DOCUMENTS

WO WO 03/082111 A1 10/2003

(Continued)

*Primary Examiner*—Tai Nguyen
(74) *Attorney, Agent, or Firm*—Fulwider Patton LLP

(57) ABSTRACT

An intelligent medical vigilance system that observes and analyzes, and, only in the event of a clinically significant negative condition, notifies and reports the event to the care staff utilizing the hospital's existing nurse call system. The device includes a bedside unit connected to a pad or coverlet with a sensor array (placed under the patient) and also to an existing hospital nurse call system via an interface. Within the physical bedside unit are a signal processor and an alarm processor that measure data and evaluate whether a clinically significant event is occurring. The bedside unit is a wall-mounted unit with a display that becomes active when an alarm condition is enabled. The sensing pad or coverlet is a thin, piezoelectric film, or other similar sensing technology, with an array of sensors sheathed in soft padding and is not directly in contact with the skin of the patient. The nurse call feature is made up of hardware, software and cabling to connect to the nurse call system already installed in the hospital or care facility. The monitoring system can also be installed in vehicles to monitor operator physiological conditions.

42 Claims, 4 Drawing Sheets

U.S. PATENT DOCUMENTS

| | | | |
|---|---|---|---|
| 5,448,996 | A | 9/1995 | Bellin et al. |
| 5,585,785 | A | 12/1996 | Gwin et al. |
| 5,590,650 | A | 1/1997 | Genova |
| 5,724,025 | A | 3/1998 | Tavori |
| 5,808,552 | A | 9/1998 | Wiley et al. |
| 5,846,206 | A | 12/1998 | Bader |
| 5,917,414 | A | 6/1999 | Oppelt et al. |
| 5,942,979 | A | 8/1999 | Luppino |
| 5,989,193 | A | 11/1999 | Sullivan |
| 6,011,477 | A | 1/2000 | Teodorescu et al. |
| 6,014,346 | A | 1/2000 | Malone |
| 6,014,602 | A | 1/2000 | Kithil et al. |
| 6,047,203 | A | 4/2000 | Sackner et al. |
| 6,050,940 | A | 4/2000 | Braun et al. |
| 6,146,332 | A | 11/2000 | Pinsonneault et al. |
| 6,160,478 | A | 12/2000 | Jacobsen et al. |
| 6,195,008 | B1 | 2/2001 | Bader |
| 6,198,394 | B1 | 3/2001 | Jacobsen et al. |
| 6,224,549 | B1 | 5/2001 | Drongelen |
| 6,248,064 | B1 | 6/2001 | Gopinathan et al. |
| 6,261,237 | B1 | 7/2001 | Swanson et al. |
| 6,280,392 | B1 | 8/2001 | Yoshimi et al. |
| 6,315,719 | B1 | 11/2001 | Rode et al. |
| 6,375,621 | B1 | 4/2002 | Sullivan |
| 6,402,691 | B1 | 6/2002 | Peddicord et al. |
| 6,445,299 | B1 | 9/2002 | Rojas, Jr. |
| 6,450,957 | B1 | 9/2002 | Yoshimi et al. |
| 6,468,234 | B1 | 10/2002 | Van der Loos et al. |
| 6,491,647 | B1 | 12/2002 | Bridger et al. |
| 6,497,658 | B2 | 12/2002 | Roizen et al. |
| 6,506,153 | B1 | 1/2003 | Littek et al. |
| 6,516,289 | B2 | 2/2003 | David |
| 6,547,734 | B2 | 4/2003 | Madsen et al. |
| 6,575,902 | B1 | 6/2003 | Burton |
| 6,579,231 | B1 | 6/2003 | Phipps |
| 6,579,242 | B2 | 6/2003 | Bui et al. |
| 6,585,645 | B2 | 7/2003 | Hutchinson |
| 6,611,206 | B2 | 8/2003 | Eshelman et al. |
| 6,616,606 | B1 | 9/2003 | Petersen et al. |
| 6,671,563 | B1 | 12/2003 | Engelson et al. |
| 6,681,003 | B2 | 1/2004 | Linder et al. |
| 6,687,424 | B1 | 2/2004 | Gerdt et al. |
| 6,723,051 | B2 | 4/2004 | Davidson et al. |
| 6,731,989 | B2 | 5/2004 | Engleson et al. |
| 6,774,797 | B2 | 8/2004 | Freathy et al. |
| 6,784,797 | B2 | 8/2004 | Smith et al. |
| 6,804,656 | B1 | 10/2004 | Rosenfeld et al. |
| 6,809,643 | B1 | 10/2004 | Elrod et al. |
| 6,821,249 | B2 | 11/2004 | Cassecells, III et al. |
| 6,822,564 | B2 | 11/2004 | Al-Ali |
| 6,822,571 | B2 | 11/2004 | Conway |
| 6,822,573 | B2 | 11/2004 | Basir et al. |
| 6,984,207 | B1 | 1/2006 | Sullivan et al. |
| 6,988,989 | B2 * | 1/2006 | Weiner et al. ............... 600/300 |
| 2003/0018241 | A1 | 1/2003 | Mannheimer |
| 2004/0111045 | A1 | 6/2004 | Sullivan et al. |
| 2004/0111296 | A1 | 6/2004 | Rosenfeld et al. |
| 2005/0159987 | A1 | 7/2005 | Rosenfeld et al. |
| 2005/0177400 | A1 | 8/2005 | Rosenfeld et al. |
| 2005/0187796 | A1 | 8/2005 | Rosenfeld et al. |
| 2005/0190068 | A1 | 9/2005 | Gentry et al. |
| 2005/0203777 | A1 | 9/2005 | Rosenfeld et al. |
| 2006/0063982 | A1 | 3/2006 | Sullivan et al. |

FOREIGN PATENT DOCUMENTS

| | | |
|---|---|---|
| WO | WO 2005/000108 | 1/2005 |

* cited by examiner

| PARAMETER 1 (P1) | PARAMETER 2 (P2) | ALARM | NOTES |
|---|---|---|---|
| A | A OR B OR C OR D OR E | YES | P1 ⇑ (HARD) |
| A OR B OR C OR D OR E | A | YES | P2 ⇑ (HARD) |
| E | A OR B OR C OR D OR E | YES | P1 ⇓ (HARD) |
| A OR B OR C OR D OR E | E | YES | P2 ⇓ (HARD) |
| B | B | YES | P1 ⇑ P2 ⇑ (SOFT) |
| B | C | NO | |
| B | D | YES | P1 ⇑ P2 ⇓ (SOFT) |
| C | B | NO | |
| C | C | NO | |
| C | D | NO | |
| D | B | YES | P1 ⇓ P2 ⇑ (SOFT) |
| D | C | NO | |
| D | D | YES | P1 ⇓ P2 ⇓ (SOFT) |

INTELLIGENT MEDICAL VIGILANCE SYSTEM

CROSS-REFERENCES TO RELATED APPLICATIONS

This application claims the benefit of U.S. Provisional Application No. 60/526,612 filed Dec. 4, 2003.

This application incorporates by reference copending U.S. application Ser. No. 09/662,006 in its entirety.

FIELD OF THE INVENTION

The present invention relates generally to monitoring systems, and more particularly has reference to intelligent medical vigilance systems used for monitoring patients, automobile drivers, or other persons whose physiological condition may undergo a change signifying a deterioration in condition, a tendency toward drowsiness, or other state that may have important consequences for that person or for others.

BACKGROUND OF THE INVENTION

Medical monitors have been in use for many years. Typically, medical monitors include patient monitors prescribed by a physician in a non-ICU setting.

While typical devices may be suitable for the particular purpose to which they address, they are not as suitable for providing an invisible "safety net" for a patient that will observe and analyze, and, only in the event of a clinically significant negative condition, notify and report the event to the care staff utilizing the hospital's existing nurse call system.

The main problem with conventional medical monitors is they are designed to respond to rapidly changing situations (found, in ICUs) and thus have a high false alarm rate. Outside the intensive care unit, these monitors are not usually connected to a remote alarm, so local alarms sound, disturbing the patient, their family and friends and the workflow of the various clinicians providing care to the patient. Many attempts have been made to make alarms more meaningful.

Another problem is that standard devices require contact directly to the patient's skin or body via cables or wires. This means constraining the patient's movement to prevent disconnecting the sensors and also creates a danger of entanglement or strangulation from the cables. Additionally, these devices are relatively expensive to purchase and somewhat complex to operate, requiring a trained individual to operate properly.

Thus, a need exists for simpler, less expensive and more accurate methods for noninvasive vital sign monitoring of significant negative conditions and reporting these events. This invention addresses these and other needs.

SUMMARY OF THE INVENTION

Briefly, and in general terms, the present invention involves a new and improved intelligent medical vigilance system for providing an invisible "safety net" that observes and analyzes a person's vital signs. Only in the event of a clinically significant negative condition will the device notify and report the event to the person or the care staff of a health care facility, utilizing, for example, a hospital's existing nurse call system. In so doing, the invention extends the vigilance capability and "reach" of the hospital clinical staff so that their resources can be more effectively applied.

The present invention has many of the advantages of the medical monitors mentioned heretofore and many novel features that result in a new intelligent medical vigilance system which is not anticipated, rendered obvious, suggested, or even implied by any of the prior art medical monitors, either alone or in any combination thereof.

In a presently preferred embodiment, by way of example and not necessarily by way of limitation, the invention generally comprises a bedside unit connected to a sensing array (placed under the patient) and to an existing hospital nurse call system via an interface. The sensing array preferably is a non-invasive piezoelectric sensing film or other similar sensing technology, with an array of sensors installed in soft padding under the bottom sheet of the patient's hospital bed. The sensing array is not directly in contact with the skin of the patient. Within the physical bedside unit are a signal processor and an alarm processor that measure the data and evaluate whether a clinically significant event is occurring.

The bedside unit is a wall-mounted unit with a display that becomes active (comes on) when an alarm condition is enabled or on command by the nurse, by touching any key. It has a number of dedicated and softkey buttons and controls for entering information, setting up specific items and interacting with the system.

The sensing array is a thin, piezoelectric film or other similar sensing technology, with an array of sensors sheathed in soft padding that is easily cleaned. It is placed in the patient's bed, under the bottom sheet (and other padding if needed), not directly in contact with the skin of the patient. It can be integrated into the mattress coverlet, if desired. The monitoring system of the present invention may also be used in chairs to monitor the state of relaxation of a subject via heart rate, blood pressure and respiration rates.

The nurse call feature is made up of hardware, software and cabling to connect to a nurse call system already installed in the hospital or care facility. The signal processor is made up of hardware and software that accepts, buffers and converts the sensor array signal from analog to digital format for subsequent processing. The alarm processor uses logic to monitor the parameter trends and determines when a negative condition is occurring. It then actuates the alarm circuitry for local and/or remote alarm. Soft alarms may be used to report adverse trends before an emergency condition arises. All alarms may interact with the existing nurse call system in the hospital.

In alternative embodiments, the intelligent medical vigilance system of the present invention can be adapted for use as a monitoring system for operators of motor vehicles, aircraft or other devices. The present invention is installed in one or more of the following regions of a motor vehicle: the seat, seatback, headrest, steering wheel, driving jacket, or a driving cap. One or more sensors may be located in each general location to provide for improved feedback. The vehicle operator may also carry a wrist attachment or a necklace with built in sensors.

The sensors in the vehicle transmit information about the patient to a central processor built into the vehicle via hardwiring or wireless technology. The processor analyzes the incoming information and outputs data as needed. The vigilance system can be used to alert drivers to approaching sleep states or other potentially hazardous physical conditions in order to reduce accidents. The sensors measure heart rate, respiration rate and movement of the vehicle operator.

Background noise signals are actively cancelled out to provide an accurate reading of the patient's heart rate, respiration rate and blood pressure. This cancellation allows the monitoring system to operate effectively in high background noise environments.

Trend information is also recorded and available for study.

The present invention provides an intelligent medical vigilance system that overcomes many of the shortcomings of the prior art devices.

In a preferred embodiment, the present invention provides an intelligent medical vigilance system for providing an invisible "safety net" for the patient that will observe and analyze, and, only in the event of a clinically significant negative condition, notify and report the event to the care staff utilizing the hospital's existing nurse call system.

In a further preferred embodiment, the invention provides an intelligent medical vigilance system that observes (monitors) multiple physiological signals without direct skin contact.

In yet a further embodiment, the invention provides an intelligent medical vigilance system that analyzes the information to determine whether the parameters are within normal limits or are tending to go in a clinically negative direction.

In a further aspect, the invention provides an intelligent medical vigilance system that reports the physiological parameters and provides a trend of them over time.

In yet a further aspect, the invention provides an intelligent medical vigilance system that notifies the nursing care staff when a consistently negative situation is detected via the existing nurse call system used in the facility.

In still a further aspect, the invention provides an intelligent medical vigilance system that persistently reminds nursing of continued violations or worsening situation until interventions are successful. This aspect provides an intelligent medical vigilance system that extends the vigilance capability and "reach" of the busy clinical staff so they can spend time where it has the best clinical effect.

In another aspect, the invention provides a sensor system within vehicles that alerts operators to dangerous physiological conditions that would impair the operator's ability to operate equipment safely.

These and other advantages of the invention will become more apparent from the following detailed description, taken in conjunction with the accompanying drawings, which illustrate, by way of example, the features of the invention.

DETAILED DESCRIPTION OF THE PREFERRED EMBODIMENTS

Figure 1:
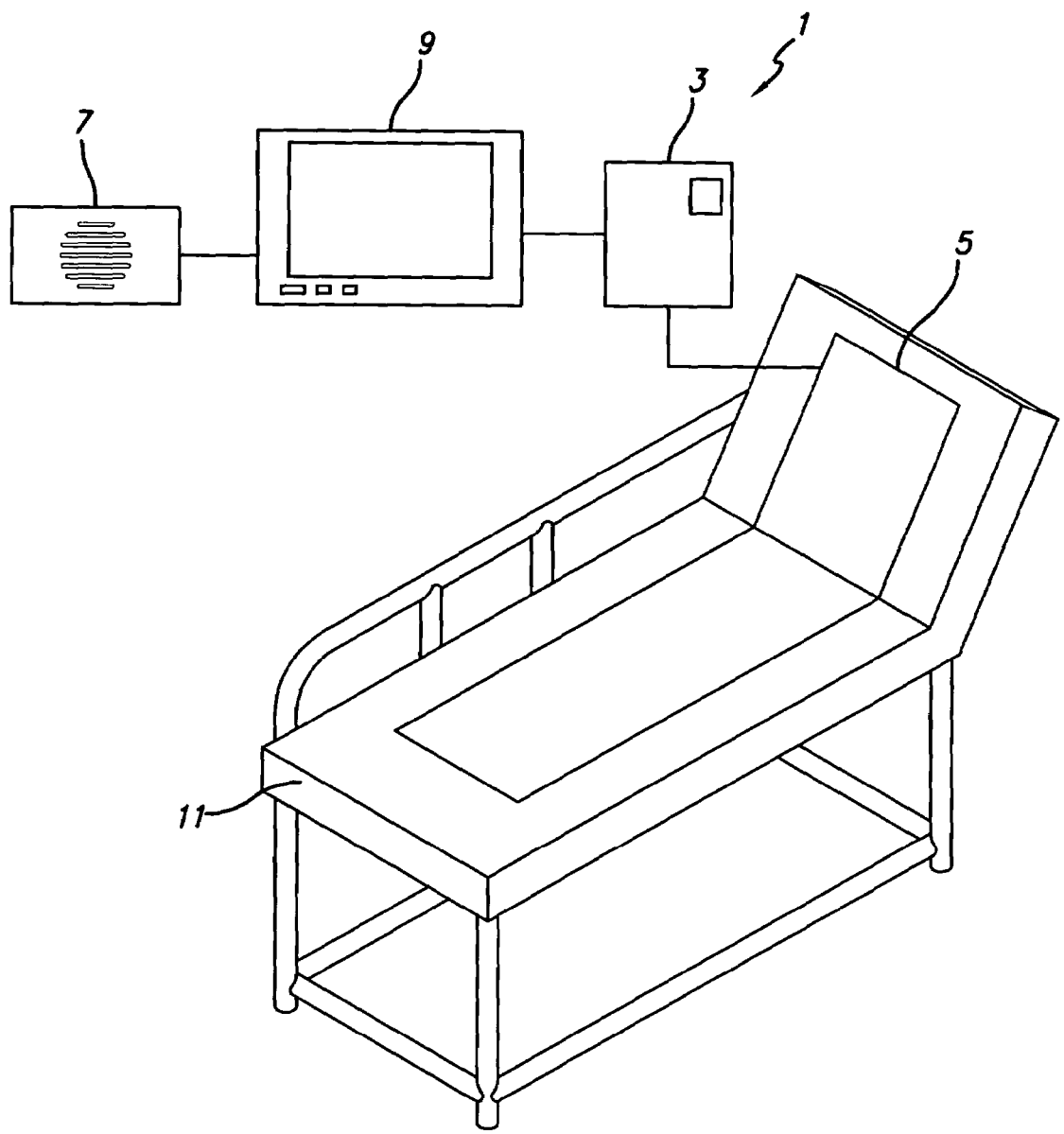
FIG. 1 is a diagram of the vigilance monitoring system of the present invention.

FIG. 1 illustrates an intelligent medical vigilance system 1, which comprises a bedside unit 3 connected to a sensing array 5 (placed under the patient) and also to an existing hospital call system 7 via an interface 9. Within the physical bedside unit 3 are a signal processor and an alarm processor that measure the data and evaluate whether a clinically significant event is occurring. The present invention can also be used as a monitoring system in vehicles.

The bedside unit 3 is a wall-mounted unit with a display 9 that becomes active (comes on) when an alarm condition is enabled or on command by the nurse, by touching any key. It has a number of dedicated and softkey buttons and controls for entering information, setting up specific items and interacting with the system.

While various types of sensors can be used, it is preferred that the sensing array 5 be in the form of a thin, piezoelectric film sensing array sheathed in soft padding that is easily cleaned. It is placed in the patient's bed 11, under the bottom sheet (and other padding if needed), not directly in contact with the skin of the patient. The sensing array 5 may be incorporated into soft padding under the bottom sheet of a patient's bed.

The nurse call feature 7 is made up of hardware, software and cabling to connect to the nurse call system already installed in the hospital or care facility.

The signal processor is made up of hardware and software that accepts, buffers and converts the sensor array signal from analog to digital format for subsequent processing. Trend information is recorded and available for study.

The alarm processor uses logic to monitor the parameter trends and determines when a negative condition is occurring. It then actuates the alarm circuitry for local and/or remote alarm. Soft alarms may be utilized to report adverse trends before emergency situation arises.

Figure 2:
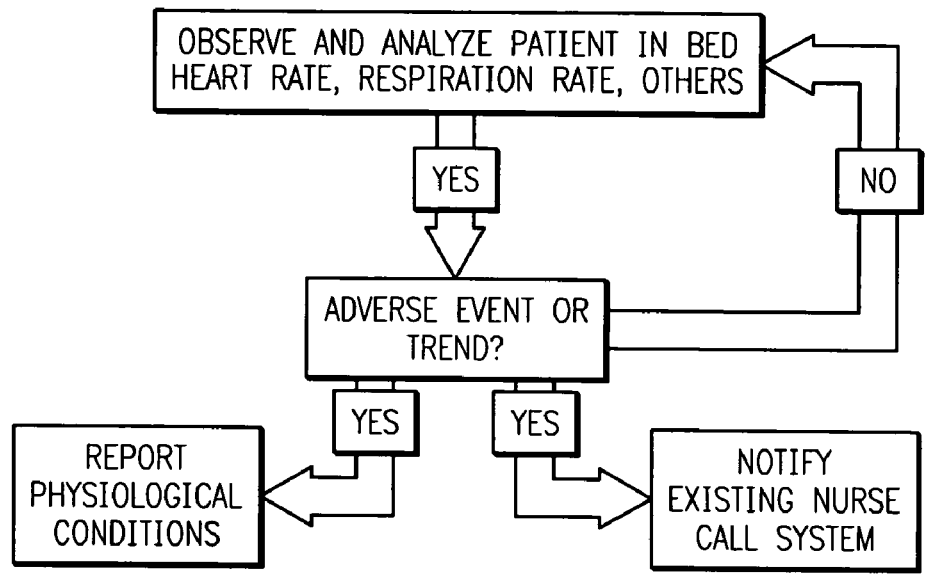
FIG. 2 is a block diagram of the system functions.
Figure 3:
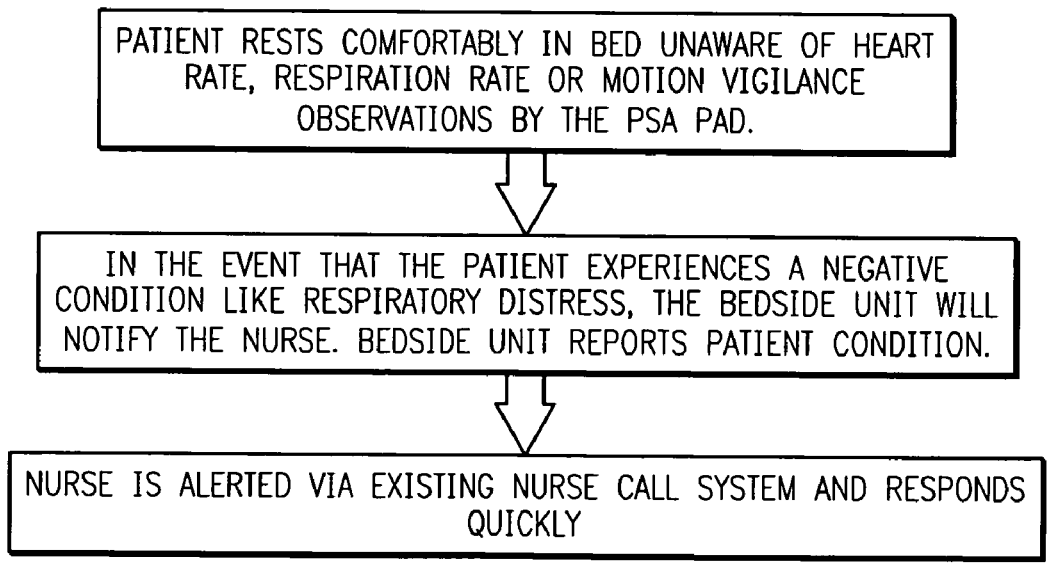
FIG. 3 is a diagram showing progression from normal patient condition to negative event and nurse response.

FIG. 2 shows a schematic diagram of the monitoring process of the present invention. FIG. 3 is a diagram showing progression from normal patient condition to negative event and nurse response.

In all patient monitoring devices with alarms the user can set "hard" alarm limits—those high and low single-parameter limits that, when passed, will cause the alarm indication, signal and tone to be transmitted to the caregiver by any number of means. The caregiver responds to correct the situation. One problem caused by such alarms is that of false positive alarms—those alarms that sound because the set threshold is passed momentarily, but that are not associated with a clinically significant event. In order to monitor the patient closely the alarm limits may be set close to the patient's present parameter value. The closer these are set, the more likely it is that a minor actual parameter variation, patient movement or other signal "noise" will make the measured parameter surpass the set alarm limit.

Few if any alarms use any delay or additional processing other that the filtering used to compute the average of and display the parameter's value. There have been many attempts to measure the inadequacy of such simple alarms in the intensive care unit. There are also methodologies used to delay alarming until a certain time since passage outside the range integrated with the extent of the deviation beyond the set range is exceeded.

In an intelligent vigilance monitor such as the one used in this invention, the "hard" alarm limits can be spread more widely than in conventional intensive care unit monitors. This is done because the patients being monitored may be relatively healthy and mobile compared to typical ICU patients. Because of their high activity level they exhibit a lot of variability in their measured vital parameters such as heart rate, respiratory rate, blood pressure, temperature, cardiac activity, etc. Thus, the clinician wants to watch over these patients' condition, but also wants to avoid false positive alarms that disrupt the patient care workflow and the feelings and outlook of the patient. However, the clinician is still interested in detecting negative trends in the patient so they can react quickly to treat or avoid deeper, more serious problems.

Figures 4, 5:
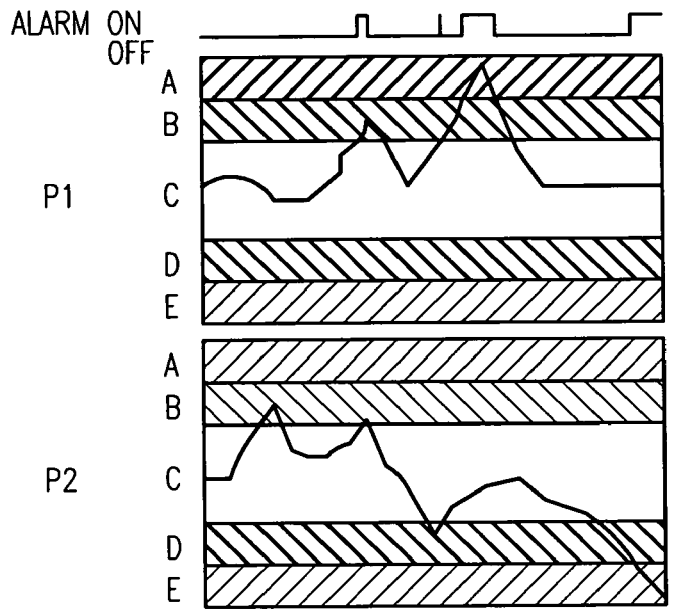
FIG. 4 is a time plot of multiple parameters, showing various parameter violations and alarm logic.
FIG. 5 is multiple parameter alarm table, showing alarm logic.

FIGS. 4 and 5 show the use of alarm limit pairs and algorithms. FIG. 4 is a time plot of multiple parameters, showing various parameter violations and alarm logic. FIG. 5 is multiple parameter alarm table, showing alarm logic.

To accomplish a balanced response, the monitor of the present invention has two or more distinct alarm limit pairs and algorithms. The purpose of the new alarm scheme is to set new thresholds within the previous "hard" limits of each parameter that will catch a patient's worsening condition prior to crossing the old single "hard" limits. This differs from just moving those limits in because these new, soft limits require that both the HR and RR values (in this example) be outside the soft limits to initiate the alarm. If either the HR or RR falls outside a hard limit, then the alarm sounds. If both the HR and RR fall outside the soft limit, but still within the hard limit, then the "soft" alarm sounds. This is best described in FIG. 4.

The parameters covered by such an alarm scheme are not limited to Heart Rate and Respiratory Rate, used in this example. In fact non-parameter-based signals (noise, motion etc.) can also be included in this logic scheme to make it more clinically valuable. In addition, the sensitivity and specificity of the "hard" alarm may be improved by using a more-complex algorithm than just "did it pass the limit?" used in many systems. This improvement could take the form of applying a number of approaches including but not limited to neural net and/or fuzzy logic.

Fuzzy logic could be applied to the limit as follows: Given one or more measurements of physiological parameters (e.g. heart rate, respiration rate, blood pressure, temperature, etc.) which require an alarm when the measurement is outside of a range (or band), a fuzzy logic type function can be defined as follows:

$$A = \sum_{n=0}^{N-1} F_n(p_n),$$

an alarm truth function, based on N different parameters or signals, and a signal truth function F(p) for each parameter or signal $$F(p) = \begin{cases} 1, & \text{for } p < t_{Ll} \\ > 0 & \text{for } t_{Ll} \leq p \leq t_{Lh} \\ 0, & \text{for } T_{Lh} < p < t_{Hl} \\ > 0, & \text{for } t_{Hl} \leq p \leq t_{Hh} \\ 1, & \text{for } p > t_{Hh} \end{cases},$$

with the additional constraint that F(p) must be monotonically increasing for $t_{H1} <= p <= t_{Hh}$ and monotonically decreasing for $t_{L1} <= p <= t_{Lh}$.

The sum of N different physiological fuzzy logic functions can be used to establish an alarm equation (See alarm truth function above) described further as follows: When A>=Ta, the alarm sounds, otherwise it does not. Ta is typically set to 0.5 if any weak (or soft) condition (or combination of weak conditions) is to cause an alarm. If Ta is set to 1.0 a strong alarm condition from at least one physiological parameter is required for the alarm to sound. If it is desired that the alarm only sound when Physiological parameters are at or above $t_{Hh}(n)$ (or below $t_{L1}(n)$), then Ta can be set to N. This method can also be used when the same physiological parameter is measured by multiple means.

In the case of two measurements of the same physiological parameter, the F(p) functions would most likely be the same for each measurement and Ta could be set to 1.0 such that if either device exceeded the $t_H$ limits, the alarm would sound. The alarm violation type (hard, soft, etc.) may be differentiated from each other or not, depending on the needs for the specific clinical application (ICU versus General Care Floor, etc.). The alarms may be set individually for each parameter as soft high and soft low or may be set by using a fixed percentage, such as 10% within the range of the hard limits for each parameter. The logic can also be extended to more than two alarms if needed.

The sensitivity of both the "hard" and "soft" limits also may be improved by delaying the alarm until the monitor determines that a signal has passed a limit for a certain length of time, such as 10 seconds. In this way, momentary changes in a signal having no clinical significance can be ignored.

Figure 6:
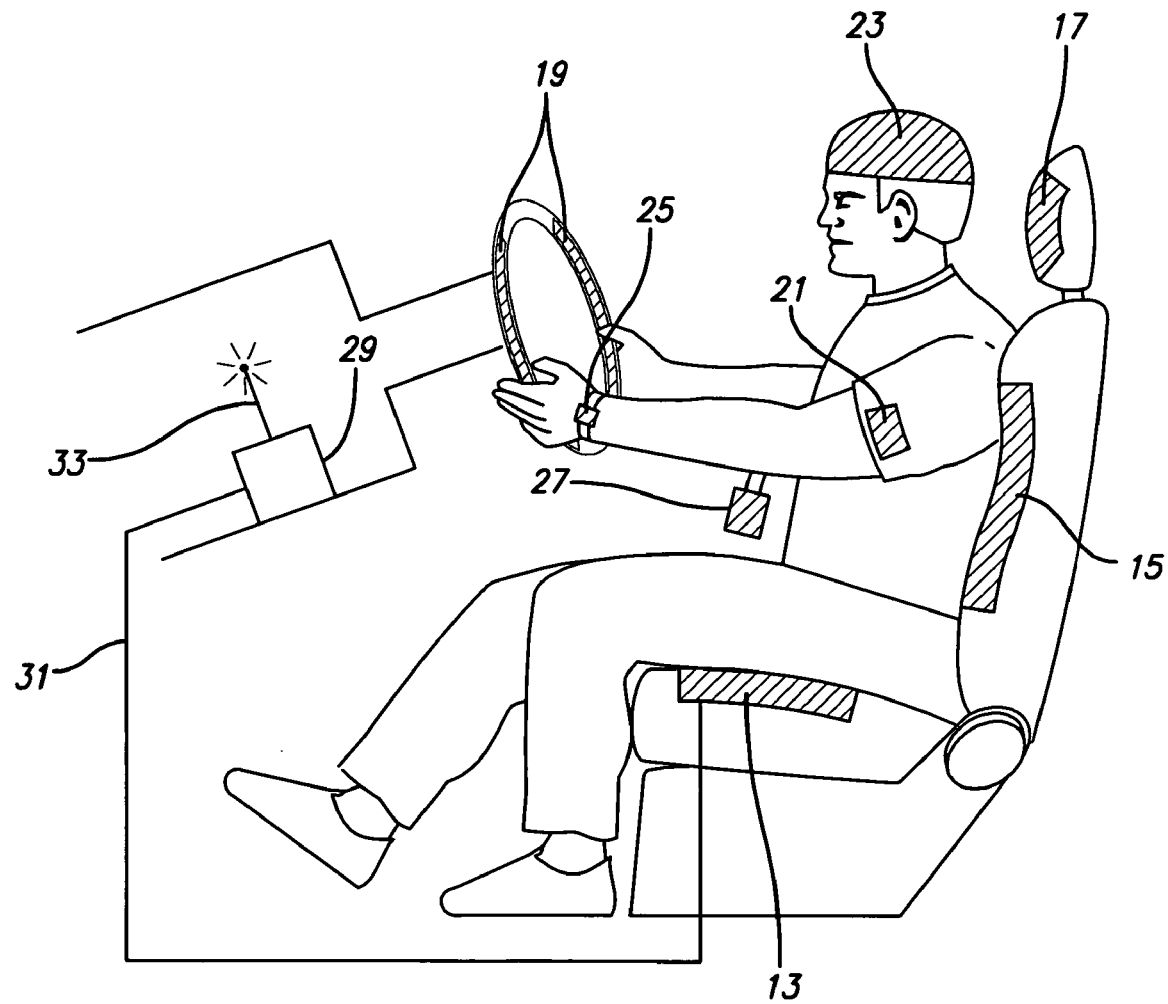
FIG. 6 is a diagram showing various configurations of sensors in a vehicle.

FIG. 6 is a diagram of the present invention installed in a vehicle. The intelligent medical vigilance system of the present invention can easily be adapted for use as a monitoring system for operators of motor vehicles, aircraft or other devices. The sensing array of the present invention is installed in one or more of the following regions of a motor vehicle: the seat 13, seatback 15, headrest 17, steering wheel 19, driving jacket 21, or a driving cap 23. One or more sensor arrays may be located in each general location to provide for improved feedback. The vehicle operator may also carry a wrist attachment 25 or a necklace 27 with built in sensor arrays.

The sensor arrays in the vehicle transmit information about the patient to a central processor 29 built into the vehicle via hardwiring 31 or wireless 33 technologies. The processor analyzes the incoming information and outputs data as needed. The vigilance system can be use to alert drivers to approaching sleep states or other potentially hazardous physical conditions in order to reduce accidents. The sensors can be configured to measure a variety of parameters, such as heart rate, respiration rate, blood pressure, temperature, cardiac output and movement of the vehicle operator. The intelligent monitoring system in vehicles uses similar alarm schemes to those in a hospital setting.

Background noise signals are actively cancelled out to provide an accurate reading of the operator's measured physiological parameters. This cancellation allows the monitoring system to operate effectively in high background noise environments.

While a particular form of the invention has been illustrated and described, it will also be apparent to those skilled in the art that various modifications can be made without departing from the spirit and scope of the invention. Accordingly, it is not intended that the invention be limited except by the appended claims.

We claim:

1. A method for monitoring the physiology of a person and providing an alarm to warn of an undesirable condition, comprising:

placing adjacent the person a plurality of sensors configured to detect physiological parameters of the person;

detecting one or more physiological parameters of the person with said sensors;
converting the detected parameters into signals;
assigning an upper hard range of signal values for each physiological parameter;
assigning a lower hard range of signal values for each physiological parameter;
assigning an upper soft range of signal values below the upper hard range for each physiological parameter, wherein the upper soft range is selected to be a predetermined downward departure from the upper hard range;
assigning a lower soft range of signal values above the lower hard range for each physiological parameter, wherein the lower soft range is selected to be a predetermined upward departure from the lower hard range;
analyzing at least two of the signals over a period of time to determine in which range each signal is situated; and
activating an alarm when at least one signal is in a hard range, and
activating an alarm when at least two signals are in a soft range.

2. The method of claim 1, wherein activating an alarm includes activating a hard alarm when at least one signal is in a hard range, and activating a soft alarm when at least two signals are in a soft range.

3. The method of claim 1, wherein activating an alarm includes activating an alarm using fuzzy logic to assess the significance of the plurality of signals in relation to the hard and soft ranges.

4. The method of claim 1, wherein each said plurality of sensors is configured to detect the same physiological parameter of the person.

5. The method of claim 1, wherein each of said plurality of sensors is configured to detect multiple different physiological parameters of the person.

6. The method of claim 1, wherein the sensors are configured to detect at least two physiological parameters selected from the group consisting of heart rate, respiration rate, blood pressure, temperature, motion, and noise emission.

7. The method of claim 1, wherein the ranges of signal values are assigned by a health care giver and can be selectively varied.

8. The method of claim 1, wherein the upper soft range is automatically selected to have a lower limit that is a predetermined percentage of the lower limit of the upper hard range, and the lower soft range is automatically selected to have an upper limit that is a predetermined percentage of the upper limit of the lower hard range.

9. The method of claim 1, wherein each parameter is assigned a different soft range.

10. The method of claim 1, wherein the magnitude of the upper soft range differs from the magnitude of the lower soft range.

11. A method for monitoring the physiology of a patient and providing an alarm to warn of an undesirable condition, comprising:
placing adjacent the patient a plurality of sensors configured to detect physiological parameters of the patient;
detecting one or more physiological parameters of the patient with said sensors;
converting the detected parameters into signals;
assigning an upper hard range of signal values for each physiological parameter;
assigning a lower hard range of signal values for each physiological parameter;
assigning an upper soft range of signal values below the upper hard range for each physiological parameter;
assigning a lower soft range of signal values above the lower hard range for each physiological parameter;
analyzing at least two of the signals over a period of time to determine in which range each signal is situated;
activating an alarm when at least one signal is in a hard range;
activating an alarm when at least two signals are in a soft range; and
communicating an activated alarm to a health care provider through a pre-existing nurse call system within a health care facility.

12. The method of claim 11, wherein activating an alarm includes activating a hard alarm when at least one signal is in a hard range, and activating a soft alarm when at least two signals are in a soft range.

13. The method of claim 11, wherein each of said plurality of sensors is configured to detect multiple different physiological parameters of the person.

14. The method of claim 11, wherein the ranges of signal values are assigned by a health care giver and can be selectively varied.

15. The method of claim 11, wherein the upper soft range is automatically selected to have a lower limit that is a predetermined percentage of the lower limit of the upper hard range, and the lower soft range is automatically selected to have an upper limit that is a predetermined percentage of the upper limit of the lower hard range.

16. A method for monitoring the physiology of a person and providing an alarm to warn of an undesirable condition, comprising:
placing adjacent the person a plurality of sensors configured to detect physiological parameters of the person;
detecting one or more physiological parameters of the person with said sensors;
converting the detected parameters into signals;
assigning an upper hard range of signal values for each physiological parameter;
assigning a lower hard range of signal values for each physiological parameter;
assigning an upper soft range of signal values below the upper hard range for each physiological parameter;
assigning a lower soft range of signal values above the lower hard range for each physiological parameter;
analyzing at least two of the signals over a period of time to determine in which range each signal is situated;
selecting signals in the upper ranges which are increasing in value and signals in the lower ranges which are decreasing in value;
activating an alarm when at least one said selected signals is in a hard range; and
activating an alarm when at least two of said selected signals are in a soft range.

17. The method of claim 16, wherein activating an alarm includes activating a hard alarm when at least one signal is in a hard range, and activating a soft alarm when at least two signals are in a soft range.

18. The method of claim 16, wherein each of said plurality of sensors is configured to detect multiple different physiological parameters of the person.

19. A method for monitoring the physiology of a person and providing an alarm to warn of an undesirable condition, comprising:
placing adjacent the person a plurality of sensors configured to detect physiological parameters of the person;

detecting one or more physiological parameters of the person with said sensors;

converting the detected parameters into signals;

assigning an upper hard range of signal values for each physiological parameter;

assigning a lower hard range of signal values for each physiological parameter;

assigning an upper soft range of signal values below the upper hard range for each physiological parameter, wherein the upper soft range is selected to be a predetermined downward departure from the upper hard range;

assigning a lower soft range of signal values above the lower hard range for each physiological parameter, wherein the lower soft range is selected to be a predetermined upward departure from the lower hard range;

analyzing at least two of the signals over a period of time to determine in which range each signal is situated; and applying a fuzzy logic function to each signal within a range;

activating an alarm when the sum of the fuzzy logic functions exceed a predetermined value.

20. The method of claim 19, wherein a first predetermined value activates a soft alarm.

21. The method of claim 19, wherein a second predetermined value activates a hard alarm.

22. The method of claim 19, wherein the ranges of signal values are assigned by a health care giver and can be selectively varied.

23. The method of claim 19, wherein the upper soft range is automatically selected to have a lower limit that is a fixed percentage of the lower limit of the upper hard range, and the lower soft range is automatically selected to have an upper limit that is a fixed percentage of the upper limit of the lower hard range.

24. A method for monitoring the physiology of a person and providing an alarm to warn of an undesirable condition, comprising:

placing adjacent the person a plurality of sensors configured to detect physiological parameters of the person;

detecting one or more physiological parameters of the person with said sensors;

converting the detected parameters into signals;

assigning a pair of upper range signal values for each physiological parameter, one of the pair being below the other, such that one range is an outer range and the other range is an inner range;

assigning a pair of lower range signal values for each physiological parameter, one of the pair being above the other, such that one range is an outer range and the other range is an inner range;

analyzing at least two of the signals over a period of time to determine in which range each signal is situated;

activating an alarm when at least one signal is in an outer range, and activating an alarm when at least two signals are in an inner range.

25. The method of claim 24, wherein activating an alarm includes activating a hard alarm when at least one signal is in a hard range, and activating a soft alarm when at least two signals are in a soft range.

26. The method of claim 24, wherein each of said plurality of sensors is configured to detect multiple different physiological parameters of the person.

27. The method of claim 24, wherein the ranges of signal values are assigned by a health care giver and can be selectively varied.

28. The method of claim 24, wherein the upper soft range is automatically selected to have a lower limit that is a predetermined percentage of the lower limit of the upper hard range, and the lower soft range is automatically selected to have an upper limit that is a predetermined percentage of the upper limit of the lower hard range.

29. Apparatus for monitoring the physiology of a person and providing an alarm to warn of an undesirable condition, comprising:

a plurality of sensors for detecting one or more physiological parameters of the person;

a processor configured to convert each detected parameter into an information signal; and an alarm system in communication with the processor, the alarm system being configured to provide one or more alarms;

wherein the processor is configured to perform steps including:

receiving a designated upper hard range of signal values for each physiological parameter receiving a designated lower hard range of signal values for each physiological parameter;

receiving a designated upper soft range of signal values below the upper hard range for each physiological parameter;

receiving a designated lower soft range of signal values above the lower hard range for each physiological parameter;

analyzing at least two signals over a period of time to determine in which range of values each signal is situated;

activating the alarm when at least one signal is in a hard range; and activating the alarm when at least two signals are in a soft range.

30. The apparatus of claim 29, further comprising an interface for connecting the alarm system to an existing nurse call system in a health care facility.

31. The apparatus of claim 29, wherein the processor is housed in a bedside unit, for placing alongside a bed for the person.

32. The apparatus of claim 31, wherein the bedside unit further comprises a display connected to the processor for displaying physiological data, the display being automatically actuated when an alarm condition occurs.

33. The apparatus of claim 31, wherein the bedside unit further comprises a display connected to a processor for displaying physiological data, the display being selectively activated by an attending health care provider.

34. The apparatus of claim 29, wherein the sensors are assembled in an array enclosed within a coverlet.

35. The apparatus of claim 29, wherein the sensors are disposed within bedding for the person.

36. The apparatus of claim 29, wherein the sensors comprise non-invasive sensors formed of piezoelectric material.

37. The apparatus of claim 29, wherein the sensors are installed in at least one location selected from the group consisting of a vehicle seat, a vehicle seatback, a vehicle headrest, a vehicle steering wheel, a driving jacket, a driving cap, a wrist attachment, and a necklace.

38. The apparatus of claim 29, wherein the processor is located in a vehicle.

39. The apparatus of claim 29, wherein the sensors transmit the detected parameters to the processor via wireless technology.

40. The apparatus of claim 28, wherein the alarm is configured to alert a driver of a vehicle of an approaching sleep state.

41. The apparatus of claim 29, wherein the sensors are configured to detect at least two physiological parameters selected from the group consisting of heart rate, respiration rate, blood pressure, temperature, cardiac output and movement of the person.

42. The apparatus of claim 29, wherein the processor is further configured such that activating the alarm includes activating a hard alarm when at least one signal is in a hard range, and activating a soft alarm when at least two signals are in a soft range.

* * * * *

UNITED STATES PATENT AND TRADEMARK OFFICE
CERTIFICATE OF CORRECTION

PATENT NO. : 7,304,580 B2 Page 1 of 1
APPLICATION NO. : 11/004589
DATED : December 4, 2007
INVENTOR(S) : Patrick K. Sullivan et al.

It is certified that error appears in the above-identified patent and that said Letters Patent is hereby corrected as shown below:

Column 4, line 53, change "that" to --than--.

Column 6, line 42, change "use" to --used--.

Signed and Sealed this

First Day of July, 2008

JON W. DUDAS
*Director of the United States Patent and Trademark Office*